US005663482A

United States Patent [19]
Prockop et al.

[11] Patent Number: 5,663,482
[45] Date of Patent: Sep. 2, 1997

[54] TRANSGENIC MICE EXPRESSING A MUTATED HUMAN COLLAGEN GENE

[75] Inventors: Darwin J. Prockop; Leena Ala-Kokko; Jaspal S. Khillan; Philipp Vandenberg, all of Philadelphia, Pa.; Sirpa Kontusaari, Oulu, Finland; Heikki Helminen, Philadelphia, Pa.; Anne Olsen, Moraga, Calif.; Boris Sokolov, Philadelphia, Pa.

[73] Assignee: Thomas Jefferson University, Philadelphia, Pa.

[21] Appl. No.: 210,063

[22] Filed: Mar. 16, 1994

Related U.S. Application Data

[63] Continuation of Ser. No. 713,945, Jun. 12, 1991, abandoned.
[51] Int. Cl.$^6$ .............................. C12N 5/00; C12N 15/00; A61K 49/00
[52] U.S. Cl. ........................... 800/2; 800/DIG. 1; 424/9.1
[58] Field of Search ............................. 800/2, DIG. 1; 424/9, 9.1

[56] References Cited

U.S. PATENT DOCUMENTS 4,736,866  4/1988  Leder et al. ............................... 800/1

OTHER PUBLICATIONS

Pereira et al (1993) J. Clin. Invest. 97, 709–716.
Helminen et al (1993) J. Clin. Invest. 92, 582–585.
Helminen et al (1993) J. Clinical Invest. 92, 582–595.
Pereira et al (1993) J. Clinical Invest. 91, 706–716.
Prockop et al., "Mutations in Human Procollagen Genes," *Structure, Molecular Biology, and Pathology of Collagen*, 580:330–339, 1990.
Slack et al., "An Upstream Regulatory Region Mediates High–Level, Tiss Specific Expression of the Human alpha1(I) Collagen Gene in Transgenic Mice," *Molel. and Cellul. Biology*, 11:2066–2074, 1991.

Bonadio et al., "Transgenic mouse model of the mild dominant form of osteogenesis imperfecta," *Proc. Natl. Acad. Sci. USA*, 87:7145–7149, 1990.

Wu et al., "Human–Mouse Interspecies Collagen I Heterotrimer Is Functional during Embryonic Development of MOV 13 Mutant Mouse Embryos," *Molel Cellul. Biology*, 10:1452–1460, 1990.

Vuorio et al., "Chondrodysplasias in Transgenic Mice Due to Mutations in the Type II Collagen Gene," *J. of Cellular Biochemistry, Supplement 15A*, 1991, Abstract B 423, p. 205.

Prockop et al. Ann. N.Y. Acad. Sci., vol. 580 (1990) pp. 330–339.

Slack et al, Mol. Cell. Biol. (Apr. 1991), vol. 11, pp. 2066–2074.

Bonadio et al, PNAS USA. (Sep. 1990), vol. 87, pp. 7145–7149.

Wu et al, Mol. Cell Biol. (Apr. 1990), vol. 10, pp. 1452–1460.

Vuorio, et al. J. Cell. Biochem. Supp 15A (Jan. 1991) p. 205, Abstract No. B 423.

Stacey et al., *Nature*, 332: 131–136 (1988).

Williams, C.J. and Prockop, D.J. (1983) *J. Biol. Chem.*, 258:5915–5921, (1983).

Ala–Kokka et al., *Proc. Natl. Acad. Sci., USA*, 87: 6565 (1990).

*Primary Examiner*—Deborah Crouch
*Attorney, Agent, or Firm*—Pennie & Edmonds; Albert P. Halluin, Esq.

[57] ABSTRACT

The invention is transgenic mice substantially all of whose cells contain a mutated human collagen gene. Methods for testing therapies for the treatment of osteogenesis imperfecta, osteoporosis, and chondrodysplasia are provided.

7 Claims, 6 Drawing Sheets

TRANSGENIC MICE EXPRESSING A MUTATED HUMAN COLLAGEN GENE

This is a continuation, of application Ser. No. 07/713,945, filed Jun. 12, 1991, now abandoned.

INTRODUCTION

This invention was made in the course of research supported in part by NIH grants AR31888 and AR39740. The Government has certain rights in this invention.

BACKGROUND OF THE INVENTION

U.S. Pat. No. 4,736,866 (Leder et al.) discloses a transgenic non-human eukaryotic animal, preferably a mouse, whose germ cells and somatic cells contain an activated oncogene sequence introduced into the animal, or an ancestor of the animal, at an embryonic stage. In a preferred embodiment, the chromosome of the transgenic animal includes an endogenous coding sequence, most preferably the c-myc gene, which is substantially the same as the oncogene sequence. Transcription of the oncogene sequence is under the control of a promoter sequence different from the promoter sequence controlling transcription of the endogenous coding sequence or under the control of a synthetic promoter sequence. Gene fusions were made using the mouse myc gene and the MMTV LTR. The MMTV-myc plasmids were digested with SalI and EcoRI and separately injected into the male pronuclei of fertilized one-cell mouse eggs. The injected eggs were then transferred to pseudopregnant mice and allowed to develop to term. At 4 weeks of age, each pup born was analyzed using DNA taken from the tail in a Southern blot analysis. The Southern blot hybridizations showed that some of the founder mice retained the injected MMTV-myc fusion. The founder animals were then mated to uninjected animals and DNA of the resulting lines of transgenic offspring was analyzed. It was found that several lines of mice carried the MMTV-myc fusion. It is taught that the animals of the invention can be used to test a material suspected of being a carcinogen by exposing the animal to the material and determining neoplastic growth as an indicator of carcinogenicity. It is also taught that the invention can be used as tester animals for materials thought to confer protection against neoplasms.

Stacey et al., Nature, 332: 131–136 (1988) disclose transgenic mice bearing an engineered mutant proα1(I) collagen gene. Two mutations were produced in a mouse COL1A1 genomic clone, both of which resulted in a substitution of a glycine residue at position 859 of the α 1(I) chain by either a cysteine or an arginine. Mutagenesis of the cloned gene was carried out by replacement of the wild-type DNA region between BstEII and SfiI restriction sites at positions 2623 and 2641 by double stranded synthetic oligodeoxyribonucleotides. The final constructs contained the complete coding region of the gene linked to one of four promoters: one-kilobase (kb), 2.5-kb and 3.7-kb fragments 5' of the mouse COL1A coding region, or the Maloney murine leukemia virus long terminal repeat promoter region. The mutant constructs were transferred into either NIH3T3 fibroblasts or into Mov13 homozygous fibroblasts which do not express the proα1(I) collagen chain. Cultured cells expressing the mutant constructs produced type I collagen with the same biochemical characteristics as mutant collagens produced by cells from patients with perinatal lethal osteogenesis imperfecta. To determine whether the mutant constructs would generate a dominant phenotype similar to the human disease, DNA from the 3.7 kb-promoter Gly-Cys mutant cosmid was microinjected into fertilized eggs which were allowed to complete development in utero. It was found that none of the mice surviving birth was positive for the transgene. In contrast, almost all of the fetuses which died shortly before or after delivery carried copies of the mutant gene suggesting that the mutant gene exerts a dominant lethal effect.

SUMMARY OF THE INVENTION

Mutations that cause synthesis of structurally abnormal proα chains of type I procollagen have been shown to cause osteogenesis imperfecta, a disease characterized by fragile bones. Similarly, it has been suggested that some variants of the subgroup of chondrodysplasia known as spondyloepiphyseal dysplasias are caused by mutations in the COL2A1 gene for type II procollagen, the precursor of the major collagen of cartilage. Moreover, mutations that cause synthesis of structurally abnormal proα chains of the type II procollagen are putatively the cause of some chondrodysplasia disease phenotypes in humans.

To investigate the effects of abnormal proα1(I) chains, a mini-gene version of the COL1A1 gene for the proα1 chain of human type I procollagen has been prepared. The 5'-half of said mini-gene extends from −2.5 kb of promoter region to intron 5 and is joined to a 3'-fragment that extends from intron 46 to 2 kb beyond the second polyadenylation site. The construct lacked a large central region containing 41 exons. All the coding sequences were in-frame and all the exons had consensus sites for RNA splices. In effect, the mini-gene was designed to synthesize shortened proα1(I) chains of type I procollagen similar to the shortened proα(I) chains I procollagen previously shown to cause lethal variants of osteogenesis imperfecta. Several lines of transgenic mice were prepared that expressed varying levels of the mini-gene product relative to the endogenous gene product. Two lines that expressed relatively low levels of the mini-gene were inbred to prepare homozygous lines, which were then crossbred to generate mice having reproducible phenotypic changes of fragile bones.

Skeletal dysplasias in man are a heterogeneous group of over 80 heritable disorders that are characterized by abnormalities in the size and shape of limbs and trunk and that usually produce individuals having short stature. Many skeletal dysplasias appear to involve defects in cartilage and, therefore, are referred to as chondrodysplasia. It has been suggested that some variants of the subgroup of chondrodysplasia known as spondyloepiphyseal dysplasias are caused by mutations in the COL2A1 gene for type II procollagen, the precursor of the major collagen of cartilage.

To investigate the effects of abnormal proα1(II) chains, a mutant version of the human COL2A1 gene for type II collagen was prepared. This mutant gene is designed to synthesize shortened proα1(II) chains of type II collagen. Several lines of transgenic mice were prepared which express varying levels of the mutated gene product. A large proportion of the mice expressing the mini-gene developed a phenotype of a chondrodysplasia. Some of the mice expressing the gene, presumably at low levels, have minimal phenotypic changes.

Methods for testing therapies for the treatment of osteogenesis imperfecta, osteoporosis, and chondrodysplasia using these transgenic mice substantially all of whose cells contain a mutated human collagen gene, such as COL1A1 and COL2A1, are provided.

BRIEF DESCRIPTION OF THE DRAWINGS

FIG. 7(A–C) shows a skeleton of a normal (left) and a transgenic (right) mouse expressing the type II mini-gene. Mineralized tissues were stained with Alizarin Red S. (A) Shows a photograph of the whole skeletons. The scale bar is 5 mm. (B) Shows an enlarged photograph of the lower skeleton of the control mouse. (C) Shows an enlarged photograph of the lower skeleton of the transgenic mouse. The scale bar is 2 mm. The transgenic mouse has shortened and thickened long bones. Also, it has delayed mineralization of tail vertebrae.

DETAILED DESCRIPTION OF THE INVENTION

It has been established that most forms of osteogenesis imperfecta (OI) are caused by dominant mutations in one of the two genes for type I procollagen. It has been suggested that mutations in the type II procollagen gene (COL2A1) are a parallel to the mutations in the two genes for type I procollagen (COL1A1 and COL1A2) that cause OI. It is reasonable, therefore, that the mutations in the type II procollagen gene recently found in probands with chondrodysplasia cause the disease phenotypes. Further, mutations in the gene for type III procollagen (COL3A1) cause some variants of type IV Ehlers-Danlos syndrome, a disease characterized by skin changes and aneurysms of the aorta. The present invention, in recognition of this remarkable fact, concerns transgenic mice expressing appropriately mutated genes for type I, type II or type III procollagen which develop phenotypic changes for OI, spondyloepiphyseal dysplasias and EDS-IV respectively. Also, the present invention concerns transgenic mice expressing a lower level of the same genes or expressing mutations of the same genes that cause less dramatic effects which develop phenotypic changes similar to human osteoporosis, osteoarthritis, and arterial aneurysms.

A mutated version of a human gene for type I collagen, the proα1(I) chain:COL1A1, that is designed so as to synthesize shortened proα1(I) chains of type I procollagen causing depletion of normal type I procollagen in tissues, was prepared. The mini-gene was injected into fertilized mouse eggs which were transferred into pseudopregnant mice, thereby producing lines of mice expressing the mutated human gene. In three instances, the mice for the first generation ($F_0$) were mosaic and phenotypically normal, but approximately one third of their offspring ($F_1$ generation) had a lethal phenotype characterized by extensive breakage of bones and other features observed in lethal variants of genetic disease in man known as osteogenesis imperfecta type II. These lines of mice expressed high levels of the mini-gene. A series of other lines expressed lower levels of the mini-gene and essentially no phenotypic changes. However, in-breeding of the mice produced homozygous mice that had fragile bones. Transgenic mice of the invention are animal models for the human diseases osteogenesis imperfecta and osteoporosis and may be useful for testing therapies for these diseases. Such transgenic animals could be useful for testing drugs and hormones advocated for the treatment of osteoporosis but whose efficacy has not yet been fully established, providing a means of developing new drugs for treatment of these diseases and as a model to study osteoporosis.

A mutated version of a human gene for type II procollagen, the COL2A1 gene that is designed so as to synthesize shortened proα1(II) chains of type II procollagen causing depletion of the normal type II procollagen in tissues, was prepared. The mini-gene was injected into fertilized mouse eggs which were transferred into pseudopregnant mice, thereby producing lines of mice expressing relatively high levels of the mutated human gene. The transgenic mice expressing the mini-gene of type II procollagen had short and thick limbs, delayed mineralization of bone, flattened facial features, a high cranial vault and a cleft palate. Further, microscopic examination of the cartilage revealed decreased density and organization of the collagen fibrils.

The transgenic chondroplasiac mice of the invention should be of considerable interest in studying the role of type II collagen in embryonic development. Also, the transgenic mice with the chondroplasia phenotype should be useful in exploring the pathoetiology and possible treatments for disorders of human cartilage. One or more of these features are seen in a variety of human chondrodysplasia. Therefore, the results provide direct proof for a causal relationship between a mutation in the COL2A1 gene causing synthesis of a structurally abnormal proα1(II) chain and a chondrodysplasia. Transgenic mice expressing lower levels of the transgene should be animal models for human osteoarthritis, since a mutation in the type II procollagen glue was recently found in a family with progressive osteoarthritis associated with a mild chondrodysplasia (Ala-Kokko et al., *Proc. Natl. Acad. Sci. USA*, 87:6565 (1990)).

The mini-genes of the present inventions have been designed to specifically deplete the type I or type II procollagen and collagen synthesized from the endogenous normal genes in mice. This correlation between depletion of collagen and a disease state was first detected in a child with osteogenesis imperfecta (Williams and Prockop, *J. Biol. Chem.* 258:5915, 1983).

Stacey et al. (1988) disclosed transgenic mice that developed a phenotype resembling lethal osteogenesis imperfecta. However, the gene employed by Stacey et al. was an amino acid substitution rather than a partial gene deletion in accordance with the present invention. Further, the gene constructs employed by Stacey et al. were constructed as oligonucleotide substitution mutations of a mouse genomic clone of the COL1A1 gene, whereas, Applicants' invention is a mini-gene constructed from two regions of the human COL1A1 gene, and a mini-gene constructed from two regions of the human COL2A1 gene. Both of the Applicants' constructs contain extensive sections of sequence deleted. The COL1A1 mini-gene construct lacks a large central region containing 41 exons and the COL2A1 mini-gene construct was designed to create a deletion that extended from intron 15 to intron 27 eliminating 12 exons of the 52 exons of the gene. By contrast, Stacey et al. teaches oligonucleotide mutagenesis of a COL1A1 genomic clone to change the coding sequence for glucine 859 to either cysteine or arginine. Stacey et al. does not teach the mutation of procollagen genes by extensive sequence deletion. Moreover, Stacey et al. were not able to develop breeding lines of mice; because all of the animals produced by Stacey et al. died, it is not possible to use such animals as models for the human disease of osteoporosis.

Gene Constructs

Figure 1:
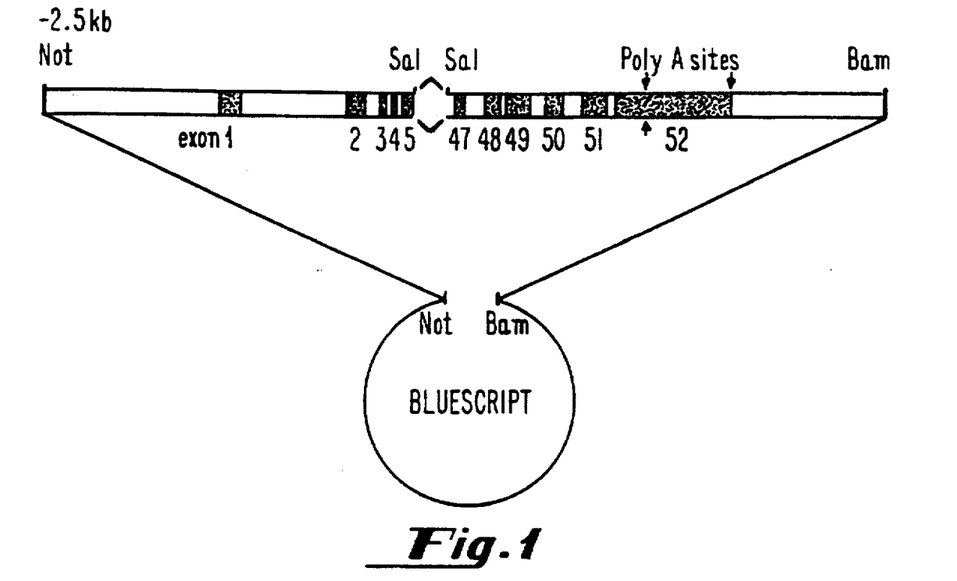
FIG. 1 shows the mini-gene construct of the proα1(I) gene. The mini-gene construct contains a SalI site joining the first five exons to the last six exons of the gene and is inserted into the Bluescript vector as a NotI/BamHI fragment.

Mini-gene and hybrid gene constructs of the human $pro\alpha1(I)$ gene were prepared. The mini-gene construct (FIG. 1) contains the first five exons and the last six exons of the gene together with 2.5 kb of the 5'-flanking sequence and 2 kb of the 3'-flanking sequence. The 5' and 3' fragments of the gene are joined through an artificial SalI site located within two intervening sequences so as not to alter any sequences required for RNA splicing. Also, all the coding sequences were in frame. The structure of the construct was verified by mapping with restriction endonucleases and showed that the 5'-end of the gene has an artificial NotI site. Thus, the construct can be excised cleanly from the plasmid vector with a NotI/BamHI restriction enzyme digestion.

Figure 2:
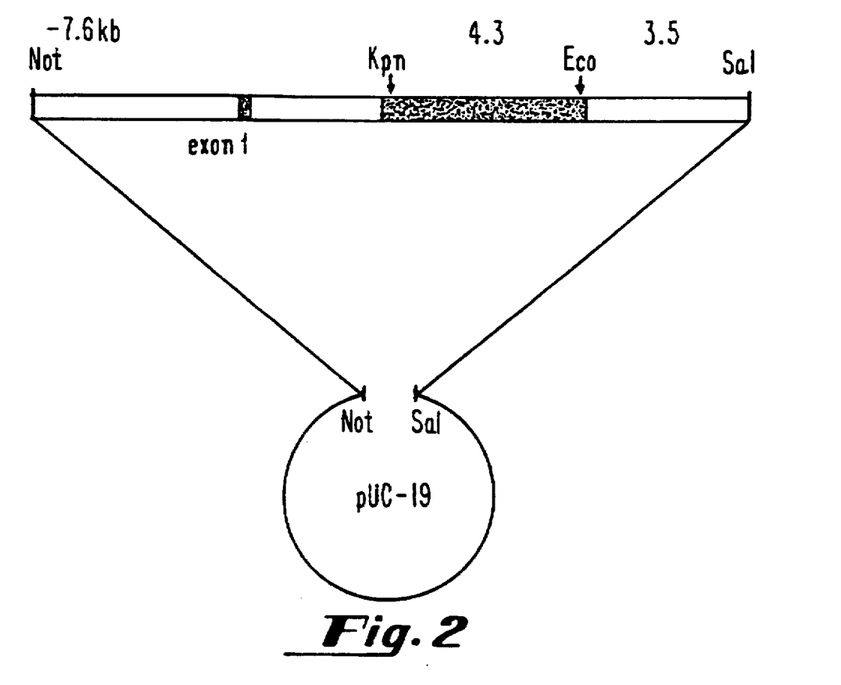
FIG. 2 shows the hybrid proα1(I) gene. This hybrid was constructed of 3 fragments: a NotI/KpnI fragment, a KpnI/EcoRI fragment, and an ECORI/SalI fragment. The hybrid construct is inserted into the plasmid vector pUC-19 as a NotI/SalI fragment.

The hybrid $pro\alpha1(I)$ gene (FIG. 2) was synthesized from three fragments: a fragment from the 5' region of the gene containing 7.6 kb of the promoter region, the first exon, the first intron and part of the second exon up to a KpnI site. The middle fragment of the gene is a 4.3 kb KpnI/EcoRI fragment from a full-length cDNA. It contains all the coding sequences from the KpnI site in exon 2 to the EcoRI site in the last exon of the gene. The 3' fragment extends from the EcoRI site for 3.5 kb into the 3' region of the gene. Artificial NotI and SalI sites were constructed at the ends of the gene so it can be excised from the plasmid vector.

Several mutated versions of the hybrid gene were prepared. One was prepared by replacing a Bst/EII restriction fragment in the hybrid gene with the same fragment from a cloned cDNA from a patient with a lethal form of OI. The patient had a single base substitution that changed the codon for glycine 904 of the $\alpha1(I)$ chain to a codon for cysteine. Site-directed mutagenesis was also used to create mutated versions of the hybrid gene. One has a single base pair change that converted the codon for glycine 886 of the $\alpha1(I)$ chain to a codon for cysteine. Other mutations include changed codons for an additional glycine (481); an X-position residue (887) and a Y-position residue (885).

Figure 6:
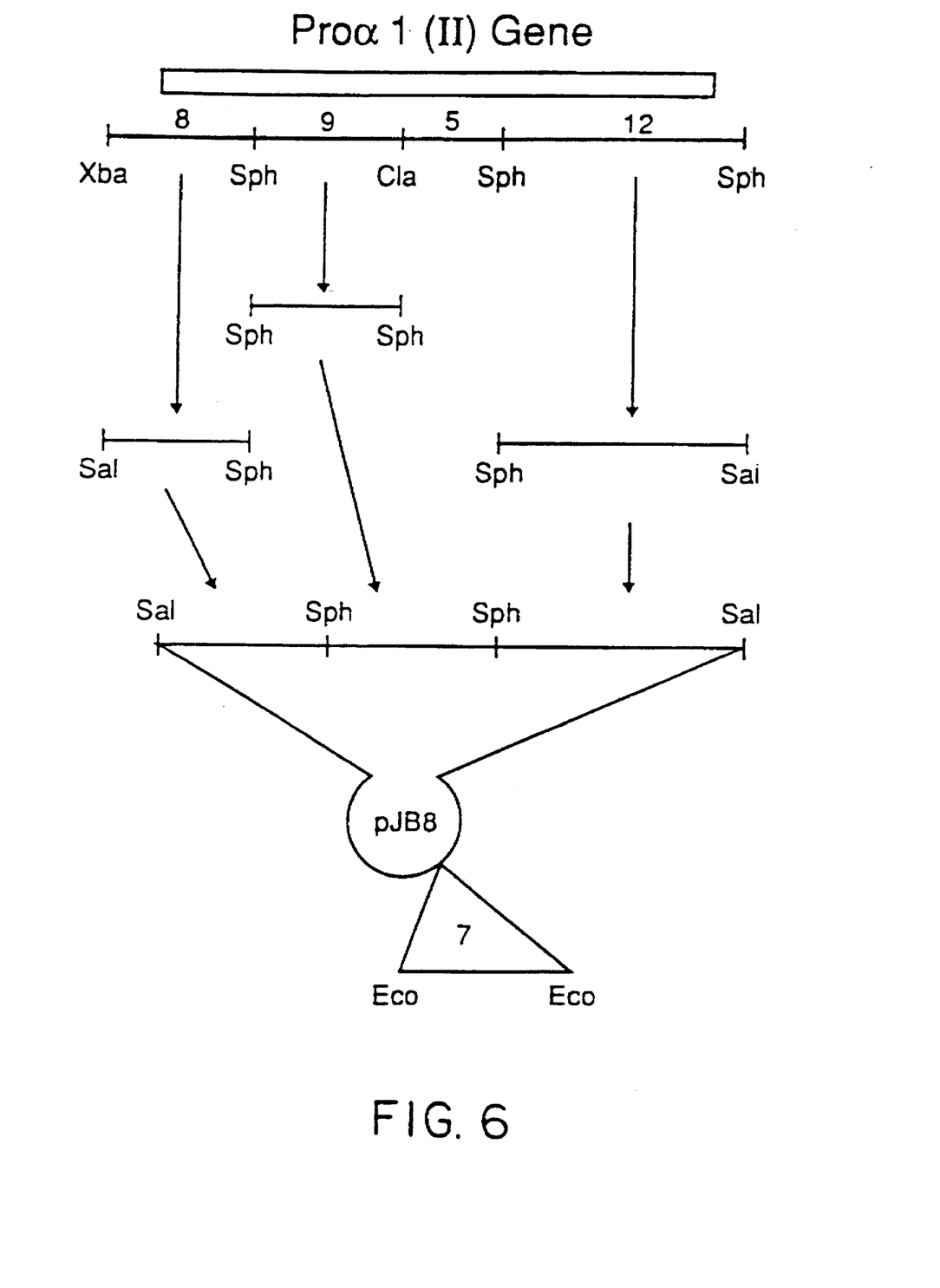
FIG. 6 shows a scheme for construction of the type II mini-gene. The gene was cleaved into four fragments and re-assembled from three of the fragments. As a result, the gene lacked 12 of the 52 exons, and 291 of the 1523 codons found in the normal gene.

Mini-gene constructs of the $pro\alpha1(II)$ gene were prepared. The gene construct was prepared from a cosmid clone containing the human COL2A1 gene. The mini-gene construct (FIG. 6) was designed so as to create a deletion that extended from intron 15 to intron 27 and eliminated 12 exons of the 52 exons of the gene. Each of the deleted exons began with a complete glycine codon for the repeating -Gly-Xaa-Yaa- sequence of the major triple-helical domain of the protein. Therefore, the partially deleted gene was in-frame in terms of both the coding sequences and the requirement for glycine as every third amino acid in a collagen triple helix. The insert in the cosmid was cleaved with XbaI, SphI and CiaI to generate four fragments ranging in size form 5 to 12 kb (FIG. 6). Three of the fragments were then assembled into a modified cosmid vector by four-way ligation. The insert was digested with SalI, electrophoresed in an agarose gel, electroeluted, extracted with phenol/chloroform/isoamyl alcohol (24:24:1), ethanol precipitated, and dissolved in 1 mM EDTA and 10 mM Tris-HCl buffer (pH 7.4) for microinjection.

Expression of the Gene Constructs in Transfected Cells

The $pro\alpha1(I)$ mini-gene was tested for expression by transfection of NIH3T3 cells by calcium phosphate precipitation. The gene was co-transfected with the neomycin gene and stable transformants of clones resistant to G418 were selected. The size of the gene predicted that correct splicing of RNA transcripts would give mRNAs of about 2.9 and 1.9 kb. Several of the clones expressed high levels of the exogenous gene as indicated by the presence of mRNA of about 1.9 kb. Similar experiments were carried out with the hybrid $pro\alpha1(I)$ gene (FIG. 2) and it was also found to be expressed at high levels in a number of prepared clones.

Transgenic Mice Expressing the Constructs

Transgenic mice expressing the $pro\alpha1(I)$ gene or modified constructs of the gene (Table 1) were prepared. In initial experiments, expression of the mini-gene was assayed by Northern blot analysis of RNA extracted from samples of tail. About half of the $F_0$ mice containing the mini-gene were found to express varying levels of the mini-gene as a shortened $\alpha1(I)$ mRNA. In subsequent experiments, it was found more convenient to assay expression by Western blot analysis with specific polyclonal antibodies. Use of a polyclonal antibody that cross-reacted with the carboxy-terminal peptide of both human and mouse $pro\alpha1(I)$ chains made it possible to assay directly the level of expression of the mini-gene relative to expression of the endogenous gene by Western blot analysis. Western blot analysis with a polyclonal antibody specific for the human N-propeptide verified the identity of the mini-gene product. The assays demonstrated that six of transgenic $F_0$ expressed the gene as shortened $pro\alpha1(I)$ chains. The level of expression in the $F_0$ mice, however, varied over a 10-fold range. Also, there was no apparent relationship between gene-copy number and the level of protein expression.

Figure 3A:
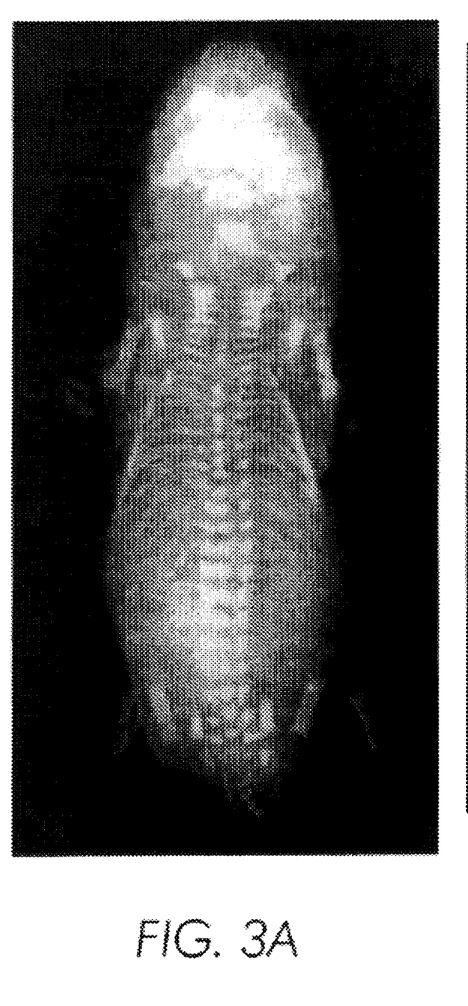
FIG. 3 shows the X-rays of a normal and a transgenic mouse expressing the type I mini-gene. On the left is the control litter mate. On the right is the transgenic mouse. The transgenic mouse has extensive fractures of bones.
Figure 3B:
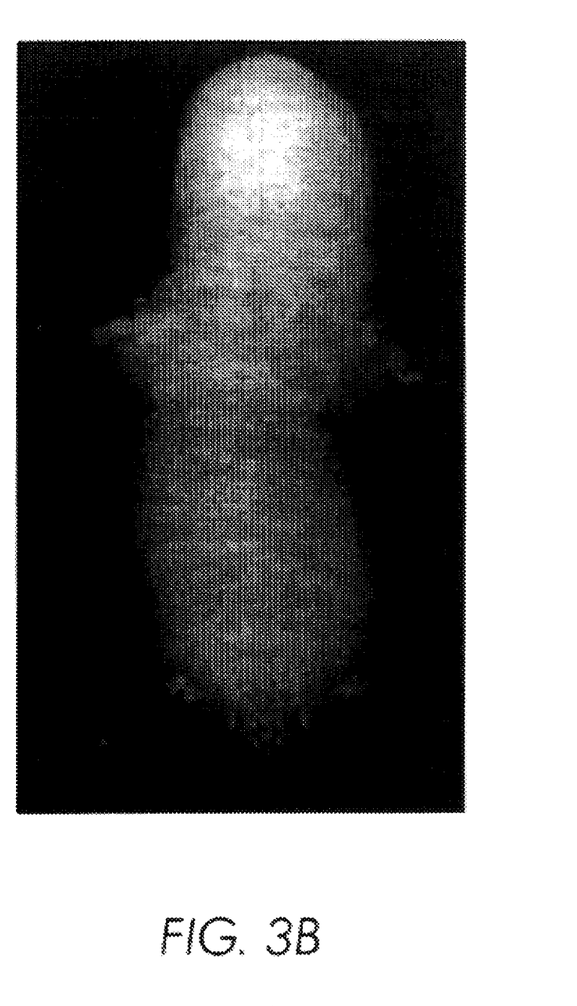
Figure 4:
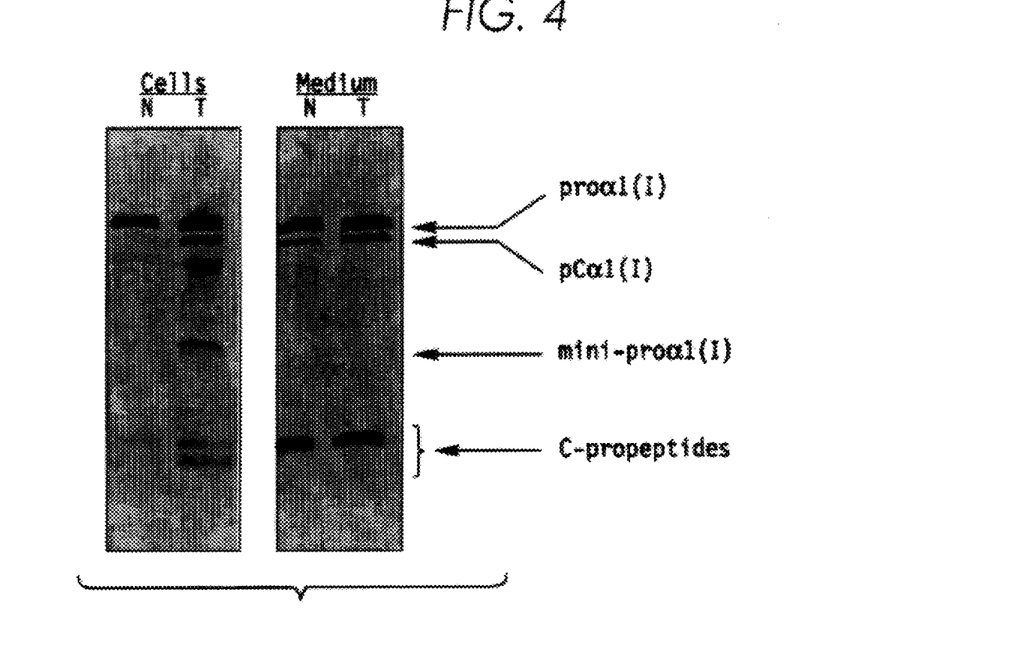
FIG. 4 shows Western blot analysis of skin fibroblasts from a normal (N) and a transgenic $F_1$ mouse of the R-line (T). The blots were reacted with the polyclonal antibodies reactive to the C-propeptides of proα1(I) chains from both human and mouse. The band marked mini-proα1(I) is a shortened proα1(I) chain synthesized from the transgene.
Figure 5:
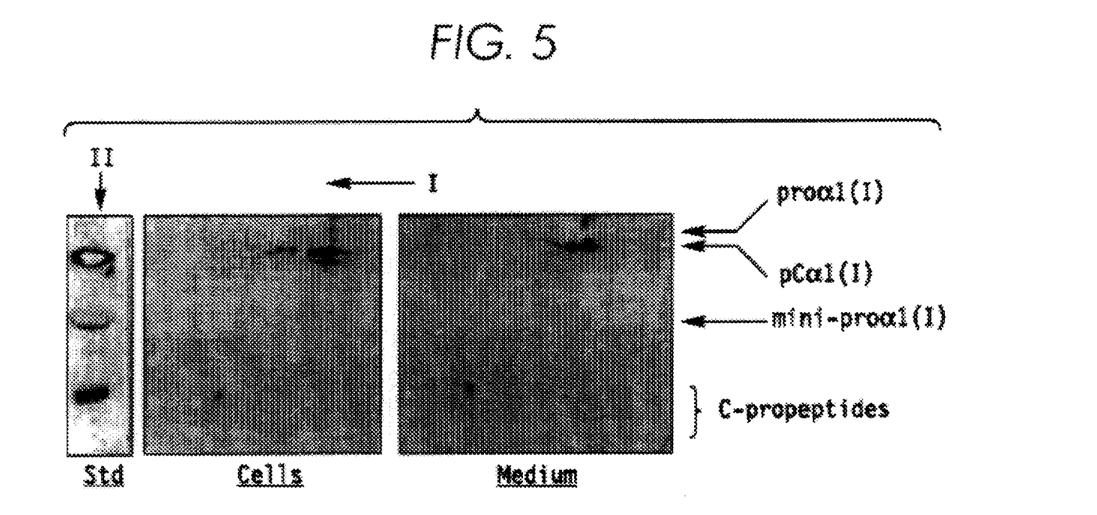
FIG. 5 shows a two-dimensional Western blot analysis of cells and medium of cultured skin fibroblasts from a transgenic mouse expressing the type I mini-gene. The samples were first electrophoresed without reduction (direction I) and then after reduction (direction II). The standard (Std) was a reduced sample of medium. The results demonstrate that the shortened proα1(I) chains [indicated as mini-proα1 (I)] became disulfide-linked to the normal proα1(I) chains synthesized from the mouse endogenous gene.

Seven $F_0$ mice were mated with wild type mice to produce $F_1$ offspring. Six of the seven $F_0$ mice transmitted the gene to their progeny (Table 1). Transgenic $F_1$ mice from two lines were normal (I-line and J-line in Table 1). In contrast, all the transgenic $F_1$ mice from three $F_0$ founders had a distinctive and lethal phenotype(K-line, R-line and U-line in Table 1). In addition, one of 18 $F_1$ mice from a fourth line (V-line) had the same lethal phenotype. The lethal phenotype consisted of death within a few minutes or hours of birth. The limbs of the mice were limp and radiograms revealed extensive fractures of long bones (FIG. 3). Also, the skulls were less extensively mineralized than in control mice. In addition, the ribs had a characteristic and symmetrically wavy appearance. Careful examination of the ribs revealed that several were fractured. The fractures of the long bones and rib deformities were also apparent after the mice were stained with Alizarin red and Alician blue to emphasize the skeletal structures.

Western blot analyses indicated that the two lines of $F_1$ mice with a normal phenotype expressed low levels of the proα1(I) mini-gene (I-line and J-line in Table 1). In contrast, two lines in which all the $F_1$ transgenic mice had the lethal phenotype expressed higher levels (K-line and R-line). $F_1$ transgenic mice from the V-line expressed intermediate levels of the mini-gene (Table 1). In the V-line, one of 18 transgenic $F_1$ mice had the lethal phenotype, six were smaller than their littermates, and 11 were apparently normal. Therefore, the lethal phenotype appeared to be related to the level of expression of the proα1(I) mini-gene.

Several observations suggested that two or three of the $F_0$ founders were mosaic for the transgene. One observation was that the $F_0$ founders had a normal phenotype, whereas all the $F_1$ transgenic mice from three lines had a lethal phenotype (K-, R- and U-lines in Table 1). Another observation suggesting mosaicism was that the level of protein expression in several tissues of $F_1$ transgenic mice of the R-line was much higher than in tail from the $F_0$ founder of the line (compare values in Tables I and II). A third observation suggesting mosaicism was that only one of 37 $F_1$ mice of the U-line inherited the transgene (Table 1.)

TABLE 1

Expression of type I Mini-Gene and Phenotypes of $F_1$ Transgenic Mice

| Line | Number of litters | Transgenic mice[a] | Lethal phenotype[b] | Level of protein expression(ratio)[c] |
|---|---|---|---|---|
| I | 3 | 5/15 | 4/5 | <0.1 |
| J | 2 | 5/15 | 4/7 | <0.1 |
| K | 2 | 3/4[d] | 3/3 | 5.1 ± 1.98 |
| R | 12 | 14/51[d] | 14/14 | 2.0 ± 0.98 |
| T | 6 | 9/51 | | |
| U | 6 | 1/37 | 1/1 | |
| V | 2 | 18/41 | 1/18[e] | 0.40 ± 0.12 |

[a]Number of transgenic mice as fraction of total $F_1$ mice.
[b]Number of mice with lethal phenotype as fraction of total $F_1$ transgenic mice. The remaining $F_1$ transgenic mice were phenotypically normal.
[c]Values are means ± S.D. for ratio of mini-proα1(I) chains to endogenous proα1(I) and pCα1(i) chains. Values for I-line and J-line are for samples of tail. Values for K-line and R-line are means ± S.D. for five tissues. Values for V-line are samples of tail from five $F_1$ mice that did not have the lethal phenotype.
[d]Three additional mice from the K-line and 31 additional mice from the R-line were not tested either because they were partially eaten by the mother or because of logistic problems in carrying out the assays.
[e]About one-third of the viable transgenic mice were small (less than 75% of mean weight of littermates).

Transgenic mice expressing the proα1(II) mini-gene construct (Table 2) were prepared. Four of the five $F_0$ founders had slightly shortened limbs but no definitive phenotype. The $F_0$ founder of the fifth line (Line 5 in Table 2) was phenotypically normal and several observations suggested that he was mosaic for the transgene: (a) the copy number in tail tissue from the $F_0$ mouse was lower than in the tail tissue from $F_1$ transgenic mice from the line, (b) all $F_1$ transgenic mice had a severe phenotype and died shortly after birth, and (c) only 19% of the progeny of the $F_0$ founders inherited the transgene (Table 2). The founder of Line 42 (Table 2) may have also been a mosaic, since only one of 30 $F_1$ mice inherited the gene. In the other lines, the absence of a distinctive phenotype in the $F_0$ founders may have been explained by its mildness or a failure to examine the mice thoroughly before maturity when the skeletal changes became less apparent.

Figure 7A:
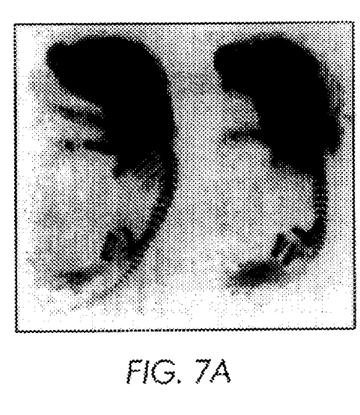
Figure 7B:
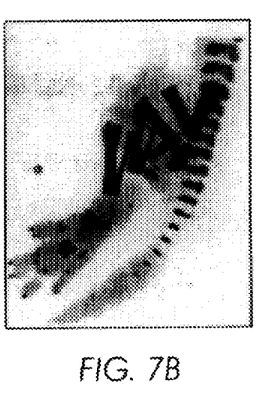
Figure 7C:
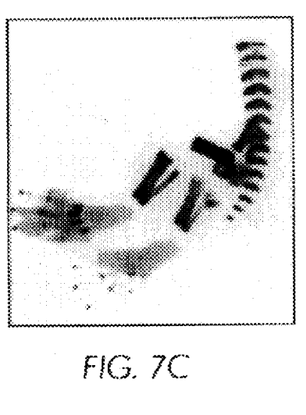
Figure 8:
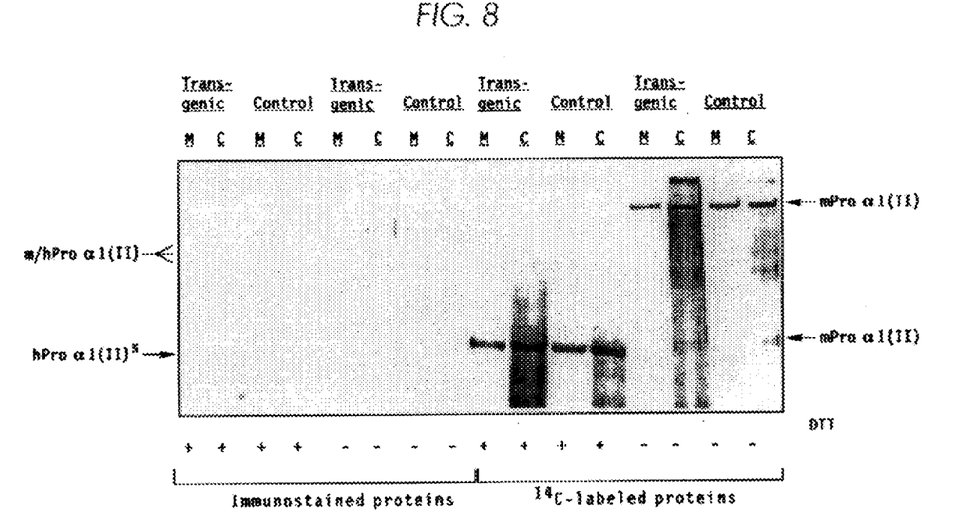
FIG. 8 shows synthesis of type II procollagen by matrix-free chondrocytes from a control littermate and a transgenic mouse. $^{14}C$-labeled proteins and immunostained proteins are of the same gel. Symbols: C, cell fraction; M, medium fraction; mProα1(II), mouse proα1(II) chains (lower band) and disulfide-linked trimers of mouse proα1(II) chains (upper band); hProα1(II)$^S$, shortened human proα1(II) chains synthesized from the transgene; DTT, with or without reduction with dithiothreitol. $^{14}C$-labeled hProα1(II)$^S$ chains are not visible, apparently because of low levels of expression.

Some of the transgenic $F_1$ mice from three separate lines (Line 5, Line 7 and Line 44 in Table 2) had the severe phenotype. The severe phenotype in each of the three lines was indistinguishable. The newborn mice were smaller than most other littermates and many died shortly after birth. X-ray films showed no air in the lungs and, therefore, death was probably caused by respiratory failure. The mice had short limbs, a short tail, a short snout and a cranial bulge (FIG. 7). Most of the pups had a wide cleft palate. Staining of the skeleton with Alizarin Red S demonstrated that the bones were short and thick compared to controls. In addition, there was delayed mineralization of bone (Table 2).

Although some of the mice from each of three lines had the same severe phenotype, there was some variability in phenotype among transgenic littermates in two of the lines. With line 7, all of the $F_1$ transgenic mice were dwarfs and showed delayed mineralization of bone. However, only one-fifth of the transgenic mice had a cleft palate (10 of 60) and only one-third died at birth or shortly thereafter (20 of 60). Several of the surviving $F_1$ transgenic mice from Line 7 had increased cervical lordosis on X-ray examination and two developed a spastic lower leg paresis, apparently secondary to the increased cervical lordosis. As expected, the incidence of the lethal phenotype increased in Line 7 when $F_2$ littermates were prepared by in-breeding of $F_1$ animals (Table 2). However, some of the $F_2$ apparent heterozygotes had no obvious cleft palate and were viable. A similar variability in phenotype was seen in Line 44 (Table 2) in that only 2 of 9 $F_1$ transgenic mice had a cleft palate and died at birth or shortly thereafter.

TABLE 2

Phenotypes of Transgenic Mice Expressing type II Mini-Gene Transgenic Mice

| Line | Generation | Transgenic mice | Gene copy number | Dwarfism[a] | Delayed mineralization[b] | Cleft palate | Dead at birth |
|---|---|---|---|---|---|---|---|
| 5 | $F_0$[c] | | 4 | 0 | 0 | 0 | |
| | $F_1$ | 25/135 | 12 | 25/25 | 25/25 | 25/25 | 25/25 |
| 7 | $F_0$ | | 2 | ± | ± | 0 | |
| | $F_1$ | 60/156 | 2 | 60/60 | 60/60 | 10/60[d] | 20/60 |
| | $F_2$[e] | 30/118 | 2,4 | 30/30 | 30/30 | 25/30[d] | 30/30 |
| 42 | $F_0$[c] | | | ± | ± | 0 | |
| | $F_1$ | 1/30 | | 1/1 | N.D.[f] | 0/1 | 0/1 |
| 44 | $F_0$ | | | ± | ± | 0 | |
| | $F_1$ | 9/14 | | 9/9 | 9/9 | 2/9[d] | 2/9 |
| 47 | $F_0$ | | | ± | ± | 0 | |
| | $F_1$ | 1/2 | | 1/1 | 1/1 | 0/1 | 0/1 |

[a]Dwarfism defined here as short and thick limbs, short snout, and cranial bulge.
[b]Delayed mineralization defined here as fewer than 10 mineralized caudal vertebrae visible in newborn mice in roentgenograms or in Alizarin Red S-stained skeletons. In control newborn mice, 11 caudal vertebrae were mineralized.
[c]Probable mosaic founder (see text).
[d]All mice with cleft palate died at birth or shortly thereafter.
[e]Mice from $F_1$ X $F_1$ matings. $F_1$ transgenic mice from Line 7 had a gene copy number of 2. Among $F_2$ transgenic mice, all mice with a copy number of 4 had the severe and lethal phenotype, but some with a copy number of 2 also had the severe and lethal phenotype.
[f]N.D. not determined.

EXAMPLES

Example 1

Preparation of Transgenic Mice

To produce transgenic mice with the proα1(I) mini-gene construct the one-cell zygotes were obtained from mating of either $F_1$ hybrid C57/BL×C$_3$H males and females, or inbred FVB/N males and females. Inbred CD1 females were used as the pseudo-pregnant recipients.

To produce transgenic mice with the proα1(II) mini-gene construct the one-cell stage mouse embryos were obtained by mating of inbred FVB/N males and females. Inbred CD1 females were used as the pseudo-pregnant recipients.

$F_1$ hybrid female mice (2 to 12 months of age) are induced to superovulate by intraperitoneal injection of pregnant mare serum (5IU) followed 48 hours later by injection of human chorionic gonadotropin (5IU). Superovulated females are subsequently mated with hybrid males (2 to 12 months of age) under conditions in which a constant light-dark cycle is maintained. Females are checked for the presence of a vaginal plug the morning after mating. Pregnant females (approximately 0.5 days post coitus) are killed by cervical dislocation. The oviducts are removed, dissected open and incubated in M2 medium containing hyaluronidase (300 ug/ml) for several minutes at room temperature to release fertilized eggs. The embryos are then transferred to M16 medium and maintained at 37° C. until needed for microinjection. DNA for injection is purified by centrifugation in CsCl and dialysis, or by agarose gel electrophoresis and electroelution after cleavage of the insert from the vector with appropriate restriction endonucleases. The fertilized eggs are injected with the DNA using a micromanipulator with a holding pipette and a microinjection pipette both attached to the stage of an inverted microscope equipped with Nomarski differential interference contrast optics. The male pronucleus is injected with about 2 picoliters of the DNA solution containing 2 µg/ml and about 600 copies per embryo of mini-gene in Tris/EDTA buffer. The eggs are transferred on the same day or cultured to the two cell stage and transferred the next day into the oviduct of a 0.5 day post-coitus pseudopregnant female.

Lines of transgenic mice that express mutated genes are cross-bred to generate lines expressing higher levels of the selected mutated gene or lines expressing more than one mutated gene.

Example 2

Assays of Expression in Transfected Cells and Transgenic Mice
Assays of DNA and RNA To assay for the presence of exogenous genes, standard Southern blotting is used (Maniatis et al., *Molecular Cloning, A Laboratory Manual*, 1982). Restriction enzymes that give different size fragments from the exogenous and endogenous gene are identified. A sample of tail or other tissue was minced in 0.1M NaCl, 0.1M EDTA and 1% SDS in 50 mM Tris-HCl buffer (pH 7.5) containing 0.7 mg/ml proteinase K and incubated with agitation at 55° C. for 8 h to 15 h. The digested sample was extracted with phenol, phenol/chloroform/isoamyl alcohol and then with chloroform/isoamyl alcohol (24:1). The DNA was ethanol precipitated and dissolved in 10 mM Tris-HCl buffer (pH 7.5) and 1 mM EDTA. The isolated DNA was digested either with EcoRI, KpnI/ClaI, or HindIII. The digested samples were electrophoresed on 0.8% agarose gel and transferred onto a nitrocellulose filter (Southern, 1975). Filters were proved with the $^{32}$P-labeled mini-gene. Copy number of the type I mini-gene in transgenic mice was assayed by simultaneously proving the filters of HindIII digested DNA with the mini-gene or a cDNA (Hf677) for the human proα1(I) chain (Bernard et al., 1983) and a cDNA (pPE18) for the mouse gene for the α2(IV) chain of type IV collagen (Kurkinen et al., 1983). The two DNA probes were mixed in equal amounts before labeling by nick translation with $^{32}$P to ensure about the same specific activity. X-ray films of the Southern blots were scanned on a densitometer to estimate the ratio of the exogenous and endogenous genes. For assay of gene copy number for the human proα1(II) mini-gene the filters were probed simultaneously with a 10 kb EcoRI-EcoRI fragment from the human gene and a 15 kb EcoRI-EcoRI fragment of the mouse gene for type II procollagen.

To assay expression of mini-genes as mRNA, standard Northern blot procedures are used (Maniatis, 1982). For RNA assays, total cellular RNA was isolated from tissues using the guanidine thiocyanate/cesium chloride procedure (Chirgwin et al., 1979). Samples containing 3 to 10 µg of RNA were electrophoresed on 1% agarose formaldehyde gels and transferred to nitrocellulose filters. To detect expression of human exogenous genes as mRNAs, probe-protection experiments or a single probe that has only selective regions of identity with mouse or human mRNAs are employed. For example, the filters were hybridized with 1.5 kb insert from Hf677, a cloned cDNA for the human proα1(I) chain (Bernard et al., 1983). Alternatively, an EcoRI/PvuII fragment of 563 nucleotides from the 5'-end of a human cDNA for the proα1(I) chain has been used in S1-nuclease probe-protection assays. The probe is fully protected by human mRNA for type I procollagen, but generates a distinctive fragment of 153 nucleotides with mouse mRNA. The probe is prepared as a single-stranded anti-sense RNA by subcloning into M13. The probe is labeled by using universal primer, the product is cleaved with restriction endonuclease, and the single-stranded probe isolated by polyacrylamide gel electrophoresis.

Assay of Protein Expression

Assays for expression of the genes at the protein level may also be performed. DNA transfected fibroblasts are taken directly for these assays. For transgenic mice, tissues were assayed directly or cultured fibroblasts or chondrocytes were prepared. For assay in mouse tissues about 50 mg of tissue was homogenized in 0.5 ml of 4M guanidine thiocyanate, 0.25M EDTA, 10 mM N-ethylmaleimide and 1 mM p-aminobenzamidine. For examination of reduced proteins, the homogenizing buffer also contained 10 mM 2-mercaptoethanol, a dithiothreitol (DDT). For examination of unreduced proteins, the buffer contained 250 mM iodoacetamide in place of the 2-mercaptoethanol or dithiothreitol (DDT). The sample was homogenized with teflon glass homogenizer and clarified by centrifugation at 13,000× g for 10 min. The sample was dialyzed against 0.15M NaCl, 10 mM EDTA, 1 mM N-ethylmaleimide, and 0.3 mM p-aminobenzamidine in 50 mM Tris-HCl buffer (pH 7.4). Aliquots of 15 µl were mixed with 15 µl glycerol and 3 µl 1% SDS and 0.0015% bromphenol blue containing either 5% 2-mercaptoethanol or 250 mM iodoacetamide. The samples were heated at 100° C. for 5 min and separated by electrophoresis on 10% polyacrylamide gel in a mini-gel apparatus (BIORAD, Protein II). The protein was electroeluted onto nitrocellulose filters and the filters were reacted with polyclonal rabbit antibodies specific for the human proα1(I) chain, specific for the human and mouse proα1(I) chain, or specific for the human proα1(II) chain. The secondary antibodies were anti-rabbit IgG coupled to alkaline phosphatase.

Cell Culturing and Labeling of Newly Synthesized Proteins

Skin fibroblasts from transgenic mice and control mice were grown at passage 5 in 25 cm$^2$ plastic flasks (Falcon Labware) in Dulbecco's modified Eagles medium with 10% fetal calf serum. At confluency, the cells were incubated for 4 h in 1.5 ml of fresh medium containing 50 µg/ml ascorbate and 10µCi/ml $^{14}$C-proline (250 mCi/mmol, Amersham Corp.). At the end of the labeling period, 0.15 ml of solution containing 250 mM EDTA, 100 mM ethylmalelmide, 10 mM phenylmethanesulfonyl fluoride and 0.1% NaN$_3$ was added to each flask to prevent proteolysis. Immediately thereafter, the media was collected and the cell layer was washed three times with 2 ml of cold phosphate-buffered saline. Media was centrifuged for 5 min at 13,000× g at 4° C. proteins were precipitated by two volumes of cold ethanol for 1 h at −20° C. The precipitate was collected by centrifugation at 13,000× g for 30 min at 4° C., washed twice with 70% cold ethanol, and vacuum dried.

Cells were recovered from the flasks by adding 2 ml of a solution containing 50 mM ethylmalelmide, 1 mM phenyl-methanesulfonyl fluoride and 0.01% NaN$_3$. The samples were incubated for 5 min at 4° C., frozen at −20° C., defrosted, scraped, transferred to a tube and vortexed. Insoluble material from lysate was removed by brief centrifugation. The supernatant was precipitated with two volumes of ethanol as described for media proteins.

For the proα1(II) mini-gene experiments with chondrocytes, joint cartilage was dissected and digested for 2 h with 1:1 (w/w) collagenase (Boehringer-Mannheim) in DMEM. Matrix-free chondrocytes obtained (typically 5×10$^5$ cells) were cultured in suspension for 4 h at 37° C. in 100 µl of the above DMEM containing 10 µCi [$^{14}$C]proline (NEN Research Products, Boston), 10% fetal calf serum (Gibco) and 5 mM EDTA. Cell proteins were recovered by a method known in the art (Williams, C. J. and Prockop, D. J. (1983) *J. Biol. Chem.*, 258:5915-5921).

Newly synthesized proα chains are analyzed by SDS-polyacrylamide gel electrophoresis before and after a series of protease digestions. For direct assay of the protein synthesized, the medium is removed, a cocktail of protease inhibitors added, and the protein precipitated with ammonium sulfate. The precipitated proteins are analyzed by SDS-polyacrylamide gel electrophoresis. Samples of cell layers are homogenized in buffer containing protease inhibitors and analyzed by SDS-polyacrylamide electrophoresis. For analysis of the proteins from transgenic mice containing the proα1(I) mini-gene, one-dimensional electrophoresis was carried out with SDS in a 4 to 15% gradient polyacrylamide gel. Two-dimensional electrophoresis may also be carried out with unreduced samples separated in one direction and reduced samples in a second direction. For two-dimensional analysis, the unreduced media or cellular proteins were first run in 7% polyacrylamide gel. Individual lanes were cut out from the first dimensional gel, treated with 5% 2-mercaptoethanol for 1 h, and separated by electrophoresis in second dimension in a 12% polyacrylamide gel. Western blot analysis with polyclonal antibodies was carried out as described above. After detection of bands using antibodies, the same blots were exposed on x-ray film to detect $^{14}$C-labeled proteins and verify the identity of the proα chains. Fluorograms of exposed films are evaluated for size of polypeptide chain synthesis, post-translational overmodification, and relative amounts of polypeptide synthesized.

Newly synthesized proα1(II) chains in cells and medium were electrophoresed in SDS-polyacrylamide gels with 3.5% stacking and 6% separating gel using a mini-electrophoresis unit Bio-Rad, Protean II).

Proα chains and procollagen synthesized by the fibroblasts are also evaluated by SDS-polyacrylamide electrophoresis after fragmentation by pepsin, vertebrate collagenase or cyanogen bromide. In the case of exogenous genes in which new codons for cysteine have been introduced, the presence of dimers will be detected by examining fragments of proα chains with or without reduction prior to electrophoresis.

Assay for Thermal Stability

To assay the helical stability of the synthesized procollagens, the medium and cell layer fractions are digested with high concentrations of a combination of trypsin and chymotrypsin at temperatures ranging from 25° C. to 43° C. for 2 minutes. Thermal stability of the triple helix is then assayed, by the recovery of α chains on SDS-polyacrylamide gel as a function of temperature.

Assay of Exogenous Gene Products by Immunoprecipitation or Western Blotting

The protein on the SDS-acrylamide gels was electroeluted onto a nitrocellulose filter. The filter was then reacted with either a polyclonal antibody specific for the N-propeptide of the human proα1(I) chain or a polyclonal antibody that reacted with the C-propeptide of the proα1(I) chain from both mouse and human (see Olsen et al., 1990). The secondary antibody was anti-rabbit IgG coupled to alkaline phosphatase (Promega Biotech). To compare the relative amounts of protein synthesized from the mini-gene and the endogenous proα1(I) gene, the Western blots prepared with cross-reacting antibodies were photocopied onto transparencies and the transparencies were assayed with a densitometer. The same filter was assayed with varying intensity settings for the photocopier in order to establish that the film response was linear. The observed values for the peaks of mini-gene and endogenous gene products per mg tissue varied with the age of the mouse, apparently because of the increase in the extracellular matrix in most tissues with age. However, values for the ratio of mini-gene product to endogenous gene product was relatively constant for transgenic mice from the same line, and repeated assays of the same sample of tissue gave a standard deviation of ±25% of mean (n=5).

Similarly, to detect the products of the proα1(II) mini-genes, proteins from the acrylamide gels were then electroblotted onto nitrocellulose and reacted with polyclonal antibodies specific for the carboxy-terminal telopeptide of the human proα1(II) chain of type II collagen. The secondary antibodies were anti-rabbit IgG coupled to alkaline phosphatase (Promega Biotech).

Example 3

Evaluation of Bones and Other Tissues in Transgenic Mice

Bone status in lines of transgenic mice is evaluated by determinations of ash weight, single photon absorptiometry, mechanical testing, staining and microradiography.

Ash Weight Determination

Bones to be determined for ash weight testing are cleaned mechanically of soft tissue and a wet weight obtained and volume obtained by displacement for significant dehydration of the bone. Dry weight and ash weights are obtained as follows: The bone is placed in a crucible and dried in a muffle furnace at 100° C. until the bone weight changes by less than a percent between determination. The bone is then incinerated in the muffle oven at 580°–600° C. for 24 hours and ash weights are obtained. Ash weight can then be described both as total ash weight and ash weight per volume (the ratio of the ash weight to the initial moist volume of the bone).

Single Photon Absorptiometry

Single photon absorptiometry is performed on a standard Lunar single photon absorptiometer with a scan speed of 0.25 mm per second. Whole bone determination and single scan line determination to specific positions along the bone are obtained from evaluation of these scans. Scans are performed by immersing the bone in water in a standard plastic tray. Polycarbonate plastic stops have been glued to the tray to allow reproducible positioning of the bone samples. Manual bone edge detection is done for final bone mass determination by single photon absorptiometry.

Skeletal Morphology and Histology

To examine the skeletal morphology of transgenic mice containing the proα1(I) mini-gene, $F_1$ mice from the R-line were stained with Alizarin red and Alizarin blue in accordance with methods known in the art.

To examine the skeletal morphology and histology of transgenic mice having the proα1(II) mini-gene construct mineralized tissue of selected newborn mice was stained with Alizarin Red S. For microscopy of tissues, whole embryos were perfused with 2% paraformaldehyde and 2.5% glutaraldehyde in 0.1M phosphate buffer (pH 7.4) shortly after birth. Tissues were decalcified by incubation in 10% EDTA (pH 7.4) for 2 to 6 days. Samples were post-fixed in 1% osmium tetroxide in 0.15 M cacodylate buffer (pH 7.4) for 2 to 4 h at 20° C., washed three times with the cacodylate buffer, and then placed in 1% tannic acid in 0.15M cacodylate buffer (pH 7.4). For polarized light microscopy, specimens embedded in paraffin were stained with Dirius Red (picrosirius staining) after incubation in xylol at 37° C. overnight and with 2 mg/ml hyaluronidase (Sigma, St. Louis) in 0.1M phosphate buffer (pH 6.9) at 37° C. overnight. The sections were analyzed with an Ortholux 2 Pol-Bk microscope (Ernst Leitz GmbH, Wetzlar, FRG) operated in monochromatic light [λ=543 nm; filter IL 543 (Schott, Mainz, FRG)] and using the de Senarmont compensation technique. For electron microscopy, samples embedded in Epon were cut into 50 to 60 nm sections, stained with uranyl acetate for 30 min and lead citrate for 2 to 4 min, and examined with a JEM-1200 EX electron microscope (Jeol ltd., Tokyo, Japan).

What is claimed:

1. A transgenic mouse whose somatic and germ cells contain at least one endogenous, normal gene for type I procollagen, and a COL1A1 mini-gene construct, wherein said mini-gene construct comprises a DNA sequence encoding the first 5 exons and the last six exons of the human proα1(I) gene operatively linked to a promoter, wherein expression of said COL1A1 mini-gene construct results in the formation of abnormalities in the skeleton of the mouse associated with osteogenesis imperfecta.

2. The transgenic mouse of claim 1, wherein said mini-gene construct further comprises 2.5 kb of the 5' untranslated region of said human proα1(I) gene.

3. A transgenic mouse whose somatic and germ cells contain at least one endogenous, normal gene for type I procollagen, and a COL2A1 mini-gene construct, wherein said mini-gene construct comprises a DNA sequence encoding the human proα1(II) gene containing a deletion from intron 15 to intron 27 and wherein said DNA sequence is operatively linked to a promoter, wherein expression of the COL2A1 mini-gene construct results in the formation of abnormalities in the skeleton of the mouse associated with chondrodysplasia.

4. A method for testing the efficacy of a compound for the treatment of skeletal abnormalities associated with osteogenesis imperfecta, comprising:

administering said compound to a mouse, wherein the somatic and germ cells of said mouse contain at least one endogenous, normal gene for type I procollagen, and a COL1A1 mini-gene construct, wherein said mini-gene construct comprises a DNA sequence encoding the first 5 exons and the last six exons of the human proα1(I) gene operatively linked to a promoter, wherein expression of said COL 1A1 mini-gene construct results in the formation of abnormalities in the skeleton of the mouse associated with osteogenesis imperfecta; and monitoring said mouse to determine the effect of said compound on said skeletal abnormalities.

5. The method of claim 4, wherein said mini-gene construct further comprises 2.5 kb of the 5' untranslated region of said human proα1(I) gene.

6. A method for testing the efficacy of a compound for the treatment of skeletal abnormalities associated with chondrodysplasia, comprising:

administering said compound to a mouse, wherein the somatic and germ cells of said mouse contain at least one endogenous, normal gene for type I procollagen, and a COL2A1 mini-gene construct, wherein said mini-gene construct comprises a DNA sequence encoding the human proα1(II) gene containing a deletion from intron 15 to intron 27 and wherein said DNA sequence is operatively linked to a promoter, wherein expression of the COL2A1 mini-gene construct results in the formation of abnormalities in the skeleton of the mouse associated with chondrodysplasia; and monitoring said mouse to determine the effect of said compound on said skeletal abnormalities.

7. The method of claim 6, wherein the chrondrodysplasia is spondyloepiphyseal dysplasia.

* * * * *